Figure 1:
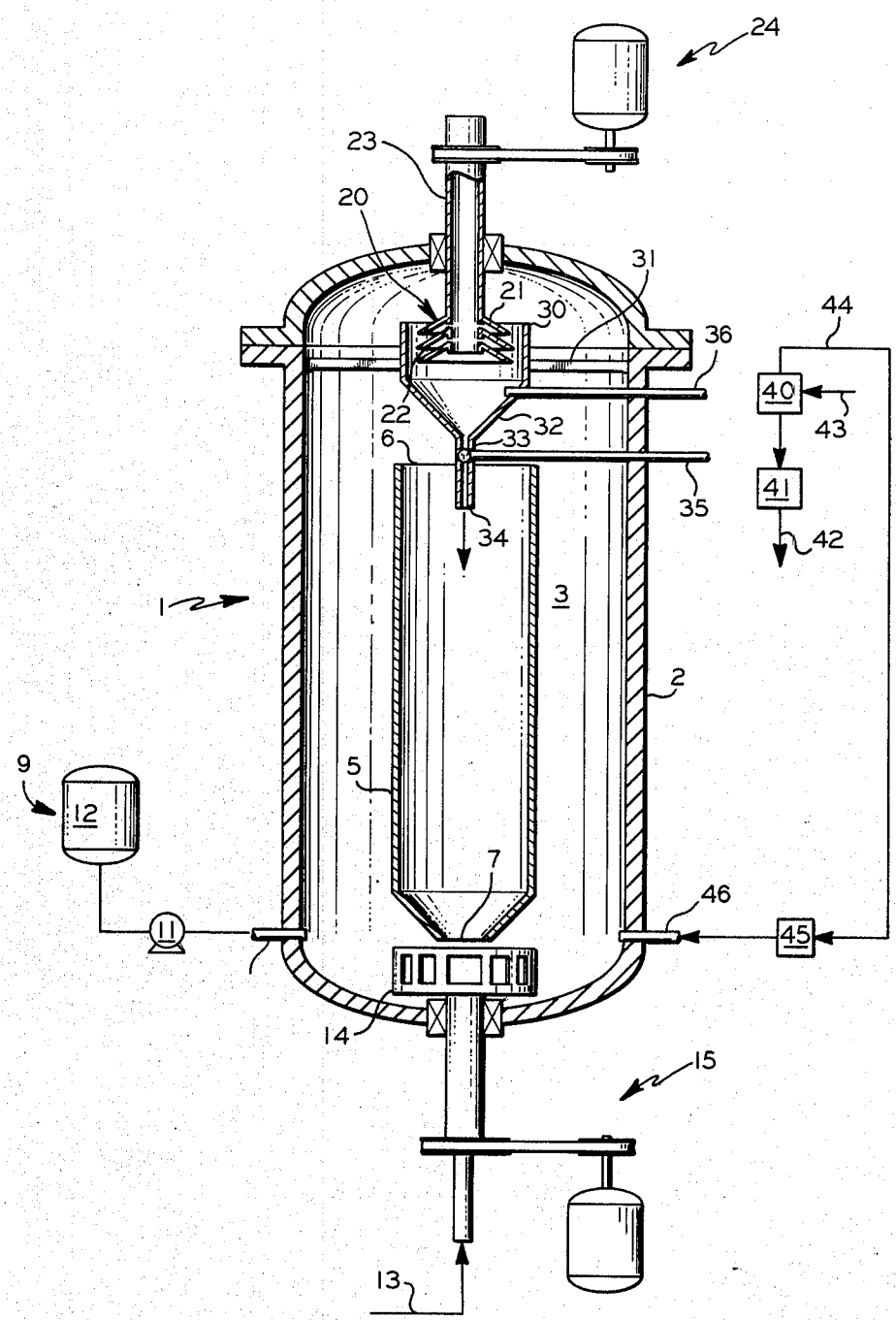

United States Patent [19]

Hitzman

[11] 4,340,677
[45] Jul. 20, 1982

[54] FERMENTATION PROCESS

[75] Inventor: Donald O. Hitzman, Bartlesville, Okla.

[73] Assignee: Phillips Petroleum Company, Bartlesville, Okla.

[21] Appl. No.: 139,371

[22] Filed: Apr. 11, 1980

[51] Int. Cl.³ .............................................. C12N 1/34
[52] U.S. Cl. .................................. 435/246; 435/261; 435/804; 435/812
[58] Field of Search .................. 435/243, 68, 246, 804, 435/261, 314, 812, 800, 315, 287; 233/13, 17, 18

[56] References Cited

U.S. PATENT DOCUMENTS 2,542,031  2/1951  Humfeld et al. .................... 435/812
3,982,998  9/1976  Hitzman et al. .................... 435/246

Primary Examiner—Raymond N. Jones
Assistant Examiner—Elizabeth J. Curtin

[57] ABSTRACT

An organism rich fluid is withdrawn from a foam fermenting apparatus by collecting and withdrawing the fluid from the foam breaker. In another embodiment the fluid from the foam breaker inside of the fermentor is subjected to a liquid/solid centrifugal action and an organism rich fluid stream as well as an organism depleted fluid stream is recovered.

10 Claims, 2 Drawing Figures

FERMENTATION PROCESS

This invention relates to phase separation of sterile mixtures. More specifically, the invention relates to a process and apparatus for separating a mixture containing a gaseous, a liquid and a solid component, particularly foams, in a system involving biological conversion of substances.

BACKGROUND OF THE INVENTION

Biological processes have been used for centuries, for instance, in the production of beer and wine. Recently, single cell protein processes have become a field of significant research among the biological processes. Whereas broadly speaking biological processes include all operations involving reactions between living materials and non living materials, in the present specification and claims a more limited definition of a biological process is used. Here a biological process is intended to refer to processes involving microorganism fermentation in a fluid environment. Such microorganisms may be, e.g. bacteria or yeasts, and such fluid environments include foam environments.

One well known biological process to which this invention is applicable is a fermentation process for the production of single cell protein. A presently preferred example for such a process is described in U.S. Pat. Nos. 3,642,578 and 3,982,998. Generally, in a single cell protein fermentation process an aerobic fermentation involving a microorganism and a nutrient fluid is carried out in the presence of free oxygen supplied for instance by the injection of air. In a fermenter generally the nutrient fluid together with the microorganism are subjected to gas injection. A foam is formed in the upper portion of the fermenter whereas the lower portion of the fermenter generally contains a liquid. The foam formed is broken in a foam breaker and from this foam breaker gas is removed whereas the fluid remains in the fermenter.

From the bottom of the fermenter a microorganism containing fluid is usually withdrawn, subjected to a solid/liquid separation step, e.g. in a wash centrifuge and the recovered washed microorganism mass is thereafter dried to obtain the final product. The fluid removed during such a solid/liquid separation step contains still valuable ingredients and is therefore generally sterilized and thereafter returned to the fermenter. In the prior art procedures the sterilization of this recycle liquid is necessary to avoid any contamination of the recycled stream. The fluid introduced into the fermenter has to be absolutely sterile in most biological processes, since the smallest contamination with living organisms in the fermenter can destroy the entire reaction and result in undesired products, and a plant shut down and thus increased costs. Therefore, it has been proposed in the art to sterilize all recycled streams. This practice is today followed throughout the industry.

THE INVENTION

It is one object of this invention to provide a new biological process and apparatus for carrying out this process.

A further object of this invention is to improve the biological process involving sterile recycle streams.

Yet another object of this invention is a simplified process for recovery of organisms from a fermenter.

A still further object of this invention is to increase the efficiency of a biological process using basically commercially available equipment.

Another object of this invention is to allow a higher steady state concentration of microorganisms in a fermentation process.

Figure 2:
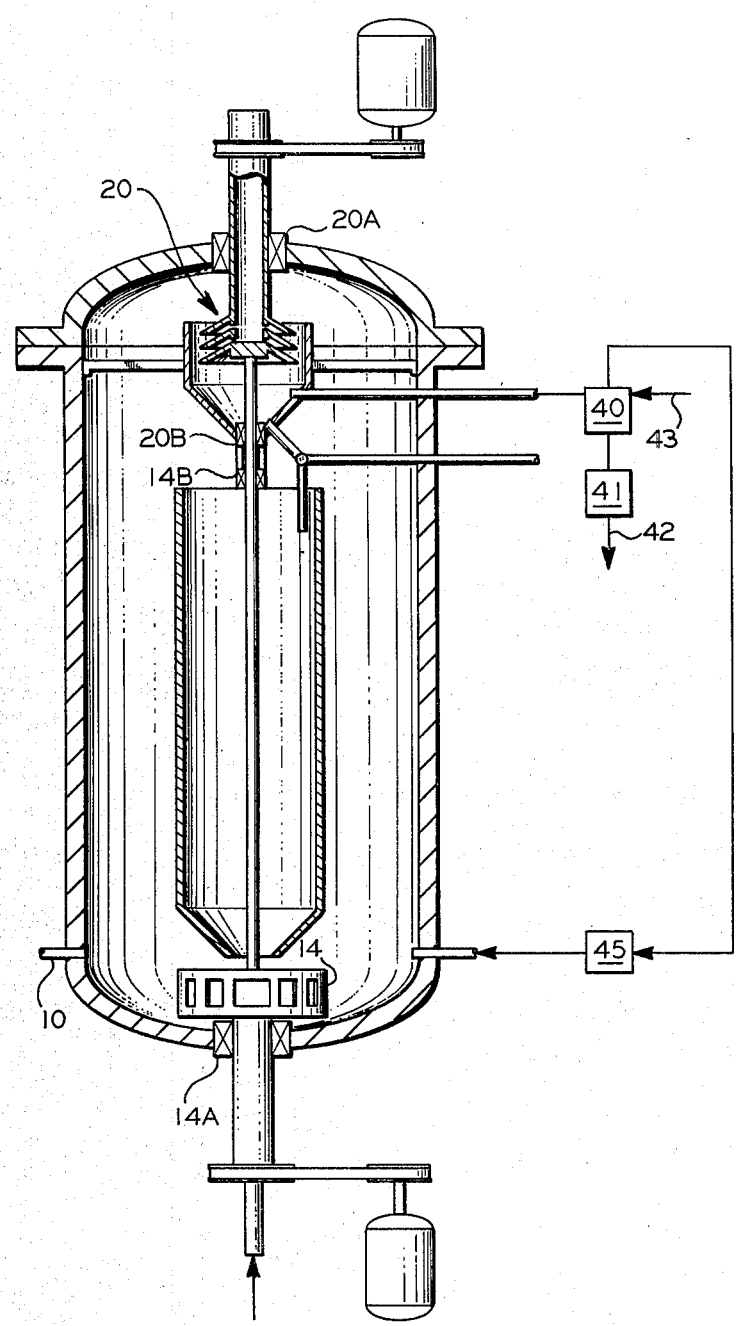

These and other objects, advantages, details, features, and embodiments of this invention will become apparent to those skilled in the art from the following description, the appended claims and the drawing in which FIG. 1 is a schematic cross sectional representation of an apparatus in accordance with this invention, and FIG. 2 is a schematic cross sectional view of another embodiment of the apparatus of the present invention.

In accordance with this invention a fermentation process is provided which distinguishes over the known processes in subjecting the fluid being essentially free of gas coming from the foam breaker to a centrifugal solid/liquid separation action within the fermenter and obtaining a first stream which is depleted of microorganism solids and a second stream which is enriched in microorganism solids.

More specifically, the present invention provides in a first embodiment an improved biological process. The biological process involves the fermentation of a multi-phase mass comprising a fluid nutrient phase, a solid organism phase and a gaseous phase. The fermentation is carried out in a fermenter where this mass is subjected to fermentation conditions thereby consuming nutrient and multiplying the organisms. The multiphase mass is present as a foam in said fermenter at least in its upper portion. The foam is subjected to a foam breaking step whereby a gas stream which is essentially free of the fluid nutrient phase and of the solid organism phase as well as a fluid stream is obtained. The fluid stream contains both the fluid nutrient phase and the solid organism phase. Frequently, the organisms concentrate in the foam and therefore the fluid stream from the foam breaking step can be slightly richer in the solid organism phase than the fluid closer to the bottom area of the fermenter.

In accordance with this invention the fluid stream from the foam breaking step is then subjected to a centrifugal action inside of said fermenter. This centrifugal action is basically a solid/liquid centrifugal action and generates a first fluid stream which is rich in the fluid nutrient phase but depleted of said solid organism phase as well as a second fluid stream which in turn is rich in said solid organism phase but depleted of said fluid nutrient phase. These two separated fluid streams in accordance with this invention can be used in a variety of recycle and control embodiments of this invention.

It is particularly preferred to pass said first fluid stream—the stream that is depleted of solids and contains the major portion of the fluid or liquid nutrient phase—directly from said centrifugal operation back into contact with microorganisms in the fermenter. It is also within the scope of this invention to pass this first fluid stream into a second fermenter. The important advantage of this invention in this embodiment resides in the fact that the reinjected fluid never leaves the fermenter or respectively never reaches any environment wherein this first fluid stream can be contaminated. The first fluid stream therefore remains entirely free of contaminating organisms and need not be sterilized again before it can be used in a fermenter again.

The organism enriched fluid stream or the second fluid stream is also biologically noncontaminated and a portion of this stream may be, if desired, introduced into a fermenter.

The process of this invention is applicable in a variety of environments. The preferred embodiment resides in an aerobic fermentation process in which the fermentation is carried out with free oxygen containing gas, such as air, being added to the mixture; other applications include nitrogen addition to the fermentation mixture as well as fermentations with no external gas addition at all wherein the culture itself forms a certain amount of gas, such as $CO_2$.

This invention can be used in biological processes for the production of ethanol, for the production of SCP or any other desired product or byproduct, such as gums. The main product stream may therefore be the solid rich or the solid depleted stream leaving the fermenter-internal centrifuge action. Water-soluble products that may thus be recovered are ethanol and gums. Ethanol withdrawal with all or at least a portion of the organisms from the internal centrifuge action remaining in the fermenter prevents the buildup of a zero-growth ethanol concentration and is therefore desirable in ethanol fermentation.

Presently, the preferred application of this invention lies in the use thereof in a SCP fermentation involving thus withdrawal of at least a portion of the solid rich material leaving the centrifuge action. Thus, the second fluid stream or the microorganism rich stream constitutes at least a portion and in some instances the entire product stream recovered from the fermenter. This stream is subjected to further recovery steps such as a washing and centrifuging step and a drying step to recover dried product. The nutrient portion of the second solid organism phase rich stream which is separated during this final workup procedure may also be reused but is preferably sterilized before any reintroduction thereof into a fermenter. Further preferred variations of this process will become apparent in connection with the description of the second embodiment of this invention, the fermentation apparatus.

In accordance with this second embodiment of the invention a fermentation apparatus is provided. This fermentation apparatus comprises a housing and at least one feed inlet into said housing and at least one product outlet from said housing. Inside of said housing a foam breaker is arranged in the upper portion thereof. A gas outlet operatively connected to this foam breaker for allowing the removal of the gas is provided for. In accordance with this invention the fermentation apparatus comprises a solid/liquid centrifuge arranged within said housing. This solid/liquid centrifuge is operatively connected to the foam breaker for receiving fluid from this foam breaker. The solid/liquid centrifuge within the housing allows to separate a solids enriched fluid stream and a solid depleted fluid stream from the centrifuge. These streams or portions thereof can directly be introduced into fermenters or reintroduced into the same fermenter without having to sterilize or purify these streams.

In a preferred variation of this embodiment of the invention the foam breaker is a mechanical foam breaker which comprises one or more solid rotatably arranged surfaces. These rotatably arranged surfaces are mechanically connectable to drive means which allow these solid surfaces to be put into rapid rotation. Foam contacting the rapidly rotating surfaces is broken and a fluid stream is spun off from the rapidly rotating surfaces. Also a gas stream is withdrawn from these surfaces. In accordance with the preferred variation of this invention here described the solid/liquid centrifuge comprises a second centrifuge surface arranged within the housing and surrounding the first solid surface. The arrangement of the second centrifuge surface around the foam breaking solid surfaces is such that the fluid spun off from these first solid surfaces of the foam breaker contacts the second centrifuge surface essentially tangentially and thus subjects this fluid which comprises solids and liquid material to a solid/liquid separation whereby the heavier solids are distributed at a higher concentration closer to the centrifuge surface. First receiving conduit means are operatively connected with the second centrifuge surface for receiving therefrom a first fluid stream rich in liquid but depleted in solids and second receiving conduit means are also operatively connected with this second centrifuge surface for receiving therefrom a second fluid stream rich in solids, but depleted in liquid.

Typically, the foam breaker comprises a plurality of axially spaced apart parallel conical surfaces connected to an axial tube with fluid connection being provided between the spaces between these conical surfaces and the interior of the axial tube. The second centrifuge surface is usually an essentially circular cylindrical surface coaxially surrounding the parallel conical surfaces leaving a small gap between the circular cylindrical surface and the wider edges of the conical surfaces of the foam breaker. The width of the gap depends largely upon the particular design of the foam breaker as well as the composition of the foam. The precise determination of the desired gap between the circular cylindrical surface and the edges of the conical surfaces is within the skill of the centrifuge designer.

Yet another variation of the apparatus embodiment of this invention provides for a funnel-type surface connected to the circular cylindrical surface constituting the solid/liquid centrifuge. This funnel-type unit is attached with its wider rim to the lower edge of the circular cylindrical surface. First conduit means are connected to an area near its center whereas the second conduit means are connected to the funnel near its upper edge. Preferably the second conduit means are arranged for a tangential withdrawal of solid enriched fluid spinning down in said circular cylindrical centrifuge.

Further details of the preferred apparatus in accordance with this invention will become apparent from the following description of the drawing.

FIG. 1 schematically and partly in cross section shows a fermentation apparatus 1. This fermentation apparatus 1 comprises a vessel 2 containing a similar fermentation or reaction zone 3 therein. The vessel 2 may be of any suitable structure including turbine type, stirred tank type and draft tube type fermenters. The latter type fermenter has mounted therein a draft tube 5 having an upper and a lower 6 and 7 respectively.

A feed supply unit 9 is operatively connected with the vessel 2 for injection of feedstock via line 10. Feedstock can be introduced via pump 11 from supply vessel 12.

Oxygen containing gas such as air can be injected into the fermentation vessel 2 via line 13 which ends within the turbine 14. This turbine 14 can be put into rapid rotation by means of motor drive 15. The rapidly spinning turbine 14 brings the oxygen in finely divided form in contact with the fluid nutrient introduced via line 10 thus generating a three phase mixture within the space 3 comprising nutrient liquid, solid microorganism and oxygen comprising gas. This three phase mixture from the lower portion to the upper portion of the ring space is formed between the vessel 2 and the draft tube 5. Near the upper end of the draft tube 5 the three phase mixture separates into a foam rising above the upper end of the draft tube 6 and a fluid stream essentially depleted of gas bubbles which circulates down through the draft tube 5 from its end 6 towards its end 7. The foam rises up further and into contact with the foam breaker 20.

The foam breaker 20 comprises a plurality of conical surfaces 21. These conical surfaces 21 are parallel to each other leaving a space between them. These spaces 22 are in fluid communication with the interior of a hollow pipe 23 to which the conical units 21 are attached. The hollow pipe 23 and the conical surfaces 21 can be put into rapid rotation by means of a motor drive unit 24.

During the operation the foam rises from the lower portion of the vessel to in the annular space between the vessel tube and the draft tube 5 from the lower portion of the fermenter toward the top. The liquid is recirculated automatically at the upper end of the draft tube 5 toward the bottom thereof. Foam rises further and finally gets into contact with the foam breaker surfaces 21. The rapidly spinning surfaces 21 break the foam and allow an essentially liquid free gas stream to leave through pipe 23. The remaining fluid comprises a liquid nutrient phase and a solid organism phase. This fluid leaves the spinning foam breaker surfaces 21.

In accordance with this invention a cylindrical centrifuge 30 is arranged surrounding the foam breaker 20. This centrifuge surface 30 preferably is arranged stationary within the vessel 2 and can be attached to the vessel 2 by means of supporting rods 31. The centrifuge cylinder 30 at the lower end thereof is attached to a funnel like cone 32. At the lower end this cone is connected via a valve 33 to two conduits 34 and 35. Neither the circumference of the centrifugal cylinder 30 and close to the lower end thereof another conduit 36 is provided for. This conduit 36 preferably is connected to the centrifugal unit 30, 32 in such a manner as to allow tangential or essentially circumferential injection or withdrawal of materials from the interior of the centrifugal unit.

During the operation of the foam breaker 20 in connection with a centrifuge 30 the fluid phase comprising the liquid nutrient phase and the solid organism phase leaving the conical surfaces 21 at a high speed and essentially in tangential direction is propelled into contact with the interior of the centrifugal cylindrical surface 30 surrounding the edges of the conical surfaces 21 in a small distance. The fluid particles therefore contact the interior of the cylindrical surface 30 and essentially a tangential direction. Thereby a fluid flow in circumferential direction along the cylindrical wall 30 of this two phase fluid is generated. This circumferential flow in turn creates a centrifugal separation or partial separation of the liquid phase and the solid phase. Thus, in the area close to the wall of the centrifugal surface 30 the solid organism phase will be enriched whereas the liquid nutrient phase depleted of solids will be flowing down in the essential portion of the centrifugal surface 30.

Depending upon the position of the valve 33 the nutrient liquid will leave the centrifugal unit 30, 32 via conduit 34 or 35. The nutrient liquid leaving through conduit unit 34 flows back into the draft tube 5 and is reused in the fermentation process. If desired, the nutrient fluid can also be removed from the fermenter via conduit 35. One of the advantages of the present invention resides in the fact that the liquid nutrient phase depleted of solid organisms can be left in the fermenter during the entire operation. This fluid therefore does not have to be resterilized in order to be again used in the fermentation.

A fluid or paste enriched in solid organisms is withdrawn from the centrifugal unit 30, 32 via conduit 36. This organism rich phase is then subjected to standard workup procedures such as a washing and separating in a washing centrifuge 40. The washed solid organism phase then is dried in a dryer 41 and finally withdrawn via line 42 as the product of the process. Wash fluid is introduced into the washing centrifuge 40 via line 43 and liquid containing the removed nutrient fluid is removed from the washing centrifuge 40 via line 44. This liquid can be reintroduced after a workup and sterilizing operation in unit 45 via conduit 46 into the fermentor 2.

It is to be noted that the cells or organisms are concentrated in the foam during the fermentation. Therefore, in accordance with one embodiment of this invention it is contemplated to withdraw the fluid comprising a liquid nutrient phase and a solid organism phase which has been collected from the foam breaker without any centrifugal enriching operation from the fermenter. Since in a foam filled fermenter the use of a foam separating device is required to allow the gas to be exhausted and to break the foam, a fluid with a high concentration of cells can be continually removed from the fermenter by collecting the spinoff fluid from the mechanical foam separating device. The solids are spun off from the mechanical foam breaker to a collecting device and this device passes the cells and the spent medium to a recovery system. The defoamed gas is vented continually. For this type of operation a collecting device is positioned so that the cells from the foam breaker spin down to a harvest valve trap which opens on command, for instance responsive to the weight load, thereby allowing the recovery of a cell concentrate. The circulation of the liquid through the draft tube is maintained for the growth of the culture. This embodiment as all the other embodiments of this invention allow the operation under stationary conditions, i.e. under conditions where the total withdrawal from the fermenter equals the total addition to the fermenter mass-wise.

Another embodiment of this invention is shown in FIG. 2. In this Figure, only the additional elements that are different from the embodiment shown in FIG. 1 have been characterized with reference numerals. In the apparatus shown in FIG. 2 the turbine 14 is supported on both sides by a bearing 14a and 14b. Similarly, the foam breaker 20 is supported by an upper and a lower bearing 20a and 20b respectively. This arrangement allows a more stable construction and operation.

Reasonable variations and modifications which will become apparent to those skilled in the art can be made in this invention without departing from the spirit and scope thereof.

I claim:

1. In a biological process involving microorganism fermentation in a fluid environment wherein a multiphase mass comprising a liquid nutrient phase, a solid organism phase and a gaseous phase in a fermenter is subjected to fermentation thereby consuming nutrient and multiplying organisms, wherein at least a portion of said multiphase mass is present as a foam in said fermenter, wherein said foam is subjected to a foam breaking step generating a gas stream essentially free of said liquid nutrient phase and of said solid organism phase which gas stream is withdrawn from said fermenter, the improvement comprising subjecting the fluid stream comprising both said liquid nutrient phase and said solid organism phase leaving said foam breaking step to a centrifugal action inside of said fermenter such as to generate a first fluid stream being rich in said liquid nutrient phase and depleted in said solid organism phase and a second fluid stream being rich in said solid organism phase and depleted in said liquid nutrient phase.

2. A process in accordance with claim 1 wherein at least a portion of one or both of said first and said second fluid streams are internally released in said fermenter into the fermentation reaction.

3. A process in accordance with claim 2 wherein a portion of said first fluid stream being liquid rich and solid depleted is passed directly from said centrifugal action inside of said fermenter to a location of release inside of said fermenter without intermediate sterilization of said portion of said first fluid stream.

4. A process in accordance with claim 1 wherein said foam breaking step is carried out inside of said fermenter by passing said foam into a mechanical foam breaker generating a fluid stream leaving said mechanical foam breaker at a high speed which fluid stream comprises both said liquid nutrient phase and said solid organism phase, and wherein said centrifugal action is carried out by contacting said high speed fluid stream with a surface shaped and arranged for subjecting the fluid stream to a centrifugal action and generating said first and said second fluid streams.

5. A process in accordance with claim 4 wherein a gas is injected into a mixture of said liquid nutrient phase and said solid organism phase in the lower portion of said fermenter such as to generate gas bubbles in said mixture and to cause circulation of the so formed three phase mixture in said fermenter comprising an upward movement of foam and a downward movement of a fluid being essentially free of gas bubbles.

6. A process in accordance with claim 4 wherein said mechanical foam breaker subjects said foam to contact with a rapidly spinning solid surface resulting in an essentially liquid and solid-free gas stream withdrawn from an axial area of said foam breaker and in said fluid stream leaving said rapidly spinning solid surface essentially tangentially with respect to the rotational movement of said solid surface and wherein said fluid stream is contacted with a centrifuge surface surrounding said rapidly spinning solid surface with a gap between said centrifuge surface, thereby subjecting said fluid stream to a centrifugal separating action generating said first and said second stream.

7. A process in accordance with claim 1 wherein (a) said second stream being rich in said solid organism phase is withdrawn from said fermenter, (b) said second stream so withdrawn is further separated into an organism product and a further liquid nutrient stream, (c) said organism product is recovered, and (d) said first fluid stream being rich in liquid nutrient phase but depleted in solid organism phase is released inside of said fermenter.

8. In a biological process involving microorganism fermentation in a fluid environment wherein a multiphase mass comprising a liquid nutrient phase, a solid organism phase and a gaseous phase in a fermenter is subjected to fermentation thereby consuming nutrient and multiplying organisms, wherein at least a portion of said multiphase mass is present as a foam in said fermenter, wherein said foam is subjected to a foam breaking step in a foam breaker generating a gas stream essentially free of said liquid nutrient phase and of said solid organism phase which gas stream is withdrawn from said fermenter, the improvement comprising collecting inside the upper portion of said fermenter at least a portion of the fluid comprising liquid nutrient phase and solid organism phase leaving the foam breaking operation at a location within a small gap of said foam breaker and withdrawing at least a portion of the so collected fluid stream from the fermenter in the vicinity of said foam breaker.

9. A process in accordance with claim 8 comprising subjecting the withdrawn fluid stream to a workup procedure, recovering a solid organism product and a liquid nutrient containing stream.

10. A process in accordance with claim 9 comprising subjecting said fluid stream withdrawn from said fermenter to a separating and cleaning operation producing a wet solid organism containing material and a nutrient containing liquid stream, drying said solid organism containing material, reintroducing at least a portion of said nutrient containing liquid stream after sterilization thereof into the fermenter.

* * * * *